US007131068B2

United States Patent
O'Neal et al.

(10) Patent No.: US 7,131,068 B2
(45) Date of Patent: *Oct. 31, 2006

(54) SYSTEM AND METHOD FOR ELECTRONIC PRESENTATIONS HAVING SIMULTANEOUS DISPLAY WINDOWS IN A CONTROL SCREEN

(75) Inventors: David Sheldon O'Neal, Dumfries, VA (US); Sean Dare Smith, Alresford (GB); Stuart Ackerman, Los Angeles, CA (US)

(73) Assignee: Learning Tree International, Los Angeles, CA (US)

( * ) Notice: Subject to any disclaimer, the term of this patent is extended or adjusted under 35 U.S.C. 154(b) by 12 days.

This patent is subject to a terminal disclaimer.

(21) Appl. No.: 10/445,322

(22) Filed: May 27, 2003

(65) Prior Publication Data

US 2004/0008221 A1    Jan. 15, 2004

Related U.S. Application Data

(63) Continuation-in-part of application No. 10/153,859, filed on May 24, 2002.

(60) Provisional application No. 60/293,179, filed on May 25, 2001.

(51) Int. Cl.
*G06F 3/00* (2006.01)

(52) U.S. Cl. .................. 715/730; 715/732; 715/733; 715/781; 715/740

(58) Field of Classification Search ................ 345/173, 345/700, 702, 723, 716–719, 730, 732, 733, 345/740, 751, 753, 764, 778, 781, 810, 970; 715/700, 702, 716–719, 723, 730, 732, 733, 715/740, 751, 753, 764, 778, 781, 810, 970
See application file for complete search history.

(56) References Cited

U.S. PATENT DOCUMENTS 4,876,657 A * 10/1989 Saito et al. .................. 345/753

(Continued)

FOREIGN PATENT DOCUMENTS

WO    WO 2005/001808 A1    1/2005

OTHER PUBLICATIONS

ABC/Disney and Keep Me Posted Blaze New Trails With California Adventure Video Mall, Nov. 10, 2000, PR Newswire.*

(Continued)

*Primary Examiner*—Lucila X. Bautista
(74) *Attorney, Agent, or Firm*—McDermott, Will & Emery

(57) ABSTRACT

An electronic presentation system and method provides multiple display screens for presentation materials as well as permits dynamic annotations to presentation materials that do not permanently alter the presentation materials. The presentation materials can easily be directed to any one of the display screens and any annotations can be saved for future use or simply deleted. A single interface screen allows simple annotation of either the left or right screen images while a zoom feature allows slides to be presented in a variety of different ways.

32 Claims, 12 Drawing Sheets

U.S. PATENT DOCUMENTS

| | | | |
|---|---|---|---|
| 5,634,018 A * | 5/1997 | Tanikoshi et al. | 345/751 |
| 5,767,897 A | 6/1998 | Howell | |
| 5,859,623 A * | 1/1999 | Meyn et al. | 345/730 |
| 5,917,480 A * | 6/1999 | Tafoya et al. | 345/732 |
| 6,008,807 A | 12/1999 | Bretschneider et al. | |
| 6,091,408 A * | 7/2000 | Treibitz et al. | 345/753 |
| 6,249,281 B1 * | 6/2001 | Chen et al. | 345/753 |
| 6,452,615 B1 * | 9/2002 | Chiu et al. | 345/776 |
| 6,714,216 B1 * | 3/2004 | Abe | 345/723 |
| 6,728,753 B1 | 4/2004 | Parasnis et al. | |
| 6,765,569 B1 * | 7/2004 | Neumann et al. | 345/419 |
| 6,789,228 B1 * | 9/2004 | Merril et al. | 715/500.1 |
| 2001/0033296 A1 * | 10/2001 | Fullerton et al. | 345/730 |
| 2002/0109712 A1 * | 8/2002 | Yacovone et al. | 345/732 |
| 2002/0140724 A1 * | 10/2002 | Qureshi et al. | 345/730 |

OTHER PUBLICATIONS

Bruce Brown, "GUIs add punch to slide presentations", 1991, PC Week, v8, n18, p. 85(5).*
Tom Negrino, "Kid Pix Studio Deluxe", 1998, Macworld, v15, n9, p. 36(1).*
Neil Randall, "Presentations on the Web", May 23, 2000, PC Magazine, p. 104-106.*
Tin Albano, SPC Shines a spotlight on presentations, Oct. 1994, PC Magazine, v 13, n17, p. 54 (1), see pp. 5-6.
PR Newswire, AT&T Combines Internet and Teleconferencing Through Interactive Web Meeting Service, Aug. 2000, see p. 4.

* cited by examiner

SYSTEM AND METHOD FOR ELECTRONIC PRESENTATIONS HAVING SIMULTANEOUS DISPLAY WINDOWS IN A CONTROL SCREEN

RELATED APPLICATIONS

This application is a continuation-in part of the U.S. patent application Ser. No. 10/153,859, filed May 24, 2002, entitled SYSTEM AND METHOD FOR ELECTRONIC PRESENTATION, which relates to and claims priority from U.S. Provisional Application Ser. No. 60/293,179, filed May 25, 2001, entitled ELECTRONIC INSTRUCTIONAL DELIVERY SYSTEM AND METHOD, the disclosure of both which are hereby incorporated in their entirety by reference.

FIELD OF THE INVENTION

The present invention relates to group presentations systems and methods and, more particularly, to an electronic presentation system and method having multiple screens.

BACKGROUND OF THE INVENTION

One traditional method for making presentations to relatively small groups, such as in an educational or training environment, includes the use of an overhead projector and view foils or transparencies. According to this familiar method, the presenter has a series of view foils that are manually placed on, and then removed from, an overhead projector in a predetermined order. While blank view foils are sometimes inserted to allow the presenter to dynamically present material during the presentation, the presenter is unlikely to annotate a previously prepared view foil because such an annotation would likely ruin the foil for future use.

Recent advances in automation have addressed some of the shortcomings of this traditional presentation method. In one instance, a computer's video output can now be connected to a projector so that a computer generated slide show can be shown on a screen, sometimes with animation. However, this introduction of automation does not change the limited and static nature of the presentation materials and methods.

Accordingly, there remains a need for a dynamic presentation system and method that allows a presenter to effectively and dynamically present material that can easily be modified and augmented according to each environment in which the presentation is made.

SUMMARY OF THE INVENTION

The present invention addresses these and other needs with a system and method that provides multiple display screens for presentation materials as well as permits dynamic annotations to presentation materials that do not permanently alter the presentation materials. The presentation materials can easily be directed to any one of the display screens, and any annotations can be saved for future use or simply deleted.

One aspect of the present invention relates to a system for providing electronic presentations in which the system includes, for example, a plurality of presentation slides stored in a first memory accessible by a programmable computer; a first display screen coupled with the programmable computer and having a first video input signal; a second display screen coupled with the programmable computer and having a second video input signal; and a third display screen coupled with the programmable computer and having a third video input signal. The presentation system also includes a presentation control software application that is stored in a second memory accessible by the programmable computer wherein the programmable computer is configured to execute the presentation control application to provide an interface, displayed on the third display screen, by which each of the plurality of slides is dispatched for display to either one of the first or second display screens. The third display screen includes a multi-windowed display interface that simultaneously depicts the current right-side image, the current left-side image and an image of the next slide to be dispatched. Using the presentation control system a presenter can selected either the right-side or left-side image and perform real-time annotation of that image.

Another aspect of the present invention relates to a software application and method for providing an electronic presentation of a plurality of slides using multiple display screens that provides a presentation control interface on a center display screen; displays a slide, from among the plurality of slides, in a preview window within the presentation control interface; receives input via the presentation control interface indicating whether to direct the slide to a right display screen or a left display screen; dispatches the slide for display on the indicated display screen; and retrieves a next slide for display in the preview window. In addition to the display on the separate screens, the presentation control interface simultaneously displays, in separate sub-windows, on the center display screen the slide from the right side, the slide from the left side, and the next presentation slide to be dispatched. From this center display screen either slide can be selected and annotated so as to modify the presentation in real-time.

BRIEF DESCRIPTION OF THE DRAWINGS

The present invention is illustrated by way of example and not by way of limitation, in the figures of the accompanying drawings and in which like reference numerals refer to similar elements and in which.

DETAILED DESCRIPTION

In the following description, for purposes of explanation, numerous specific details are set forth in order to provide a thorough understanding of the present invention. It will be apparent, however, to one schooled in the art that the present invention may be practiced without these specific details. In other instances, well-known structures and devices are shown in block diagram form in order to avoid unnecessarily obscuring the present invention.

Various embodiments of the present invention are presented and discussed below. In particular, many embodiments are described in reference to the specific environment of instructional or training presentations. This specific environment is helpful in describing many of the aspects of the present invention. However, the present invention is not limited to only this specific environment, but rather contemplates within its scope other presentation environments in which multiple screens and dynamic annotation capability are beneficial.

Figure 1:
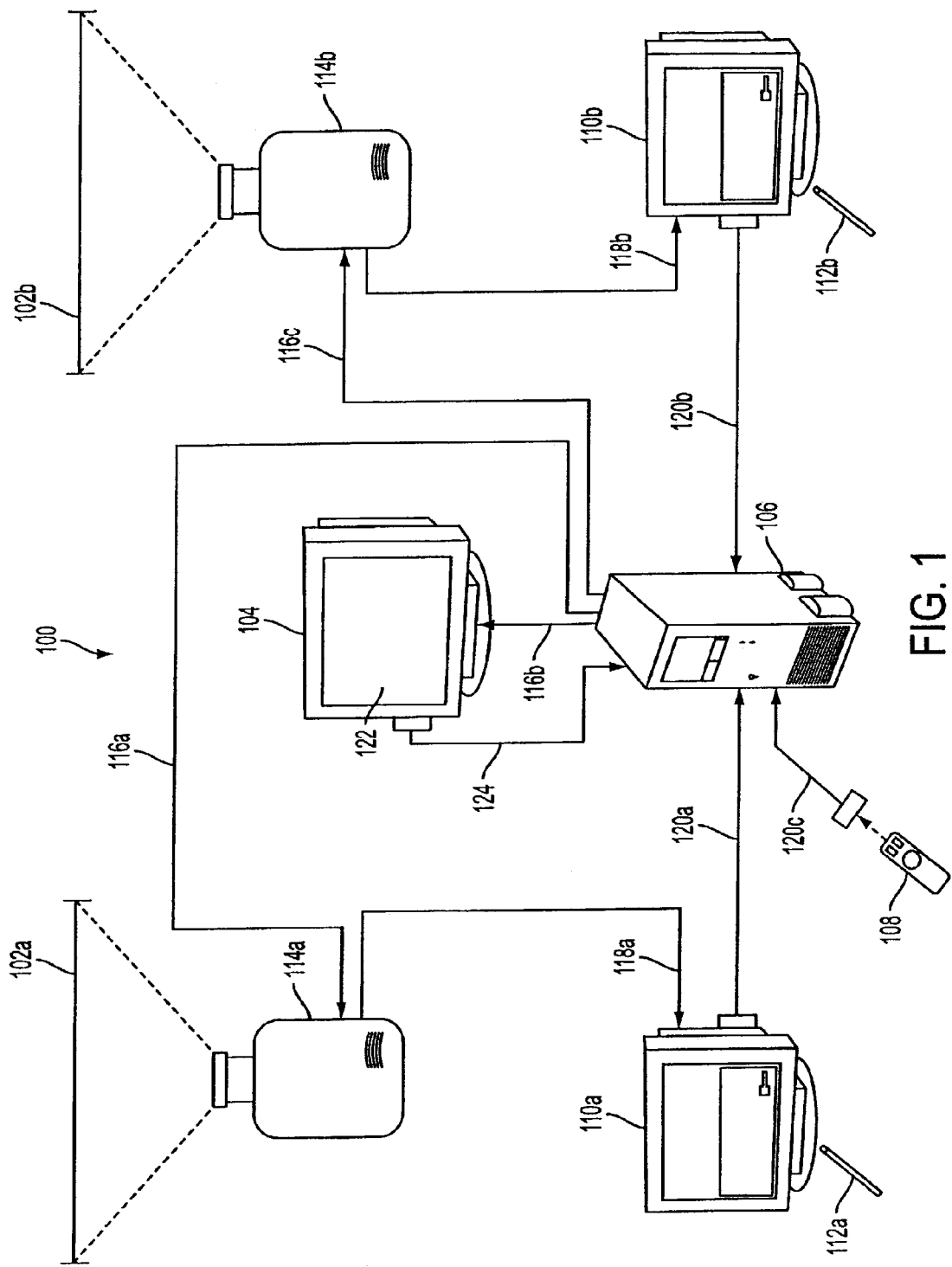
FIG. 1 illustrates an exemplary presentation system according to an embodiment of the present invention.

FIG. 1 illustrates an exemplary presentation system 100 according to one embodiment of the present invention. According to this embodiment, a computer system 106 controls the data flows and presentation materials used by the other components. In particular, the computer 106 provides a graphical interface 122 on the monitor 104 to assist the presenter in controlling a presentation. The video data displayed on the interface monitor 104 is provided by video output 116b of the computer 106. Although not shown in its entirety, computer system 106 is a conventional system in that it comprises a keyboard, mass storage devices, and network, parallel, and serial interfaces as well as the many other peripherals and components known to be part of a typical computer system.

The computer system 106 also includes separate video outputs 116a, 116c that respectively provide video output to the left-hand projector 114a and right-hand projector 114b. The video output can be SVGA formatted video signals as well as other conventional video formats. Within the present description, the left/right hand convention is from the perspective of the presenter. The video data that is output over each of the video outputs 116a, 116c is determined by the presenter using the interface 122. Using the interface 122, the presenter retrieves presentation material from storage (not shown) accessible by the computer system 106 and then directs that material to one, or both, of the video outputs 116a, 116c. The projectors 114a, 114b then display the respective presentation materials on a respective screen 102a, 102b.

The video outputs 116a, 116c, in addition to being directed to projectors 114a, 114b, also are directed via respective paths 118a, 118b to touch-screen monitors 110a, 110b. In practice, the monitors 110a, 110b would be located near the presenter while the screens 102a, 102b would be located for convenient viewing by an audience receiving the presentation. Each of the touch-screen monitors 110a, 110b are connected to the computer system 106. In FIG. 1, these connections 120a, 120b are depicted as serial connections, but other functionally equivalent feedback connection paths are contemplated by the present invention as well. These connection paths can be other types of input/output protocols and hardware and are not limited to RS-232 serial communication paths. The connections 120a, 120b are used to provide feedback from a respective touch-screen monitor 110a, 110b that indicates any tactile interaction that may be taking place with the monitors 110a, 110b. While FIG. 1 depicts an exemplary stylus 112a, 112b for each monitor 110a, 110b, tactile interaction with the monitors 110a, 110b can occur using the same stylus or even no stylus at all.

The interface 122 can be controlled using a keyboard, mouse or other input device connected to the computer 106. However, to provide the presenter some flexibility in movement and location around a room, a remote control device 108 is also connected 120c to the computer system 106 to control the interface 122 as well. This remote control device 108 could include a transmitter (and receiver on the computer 106) that utilizes USB, FireWire, IrDA, serial or many other types of input/output conventions to connect with the computer 106. Additionally, the display device 104 can also be a touch-screen device that allows the presenter to control the presentation using tactile initiated commands and such a device will need its own feedback path 124.

Within the exemplary presentation system 100 of FIG. 1, the computer system 106 controls the operation of the presentation by concurrently executing: a) a presentation interface 122 that is used to retrieve and direct (or dispatch) presentation materials to one of two video outputs 116a, 116c; b) an annotation tool for the left-hand screen 102a that receives tactile feedback from a touch-screen monitor 110a and adjusts the video output 116a accordingly; and c) an annotation tool for the right-hand screen 102b that receives tactile feedback from a touch-screen monitor 110b and adjusts the video output 116c accordingly.

Within the embodiment just described, as well as other embodiments described herein, the exemplary components are not intended to limit the scope of the present invention. For example, the touch-screen monitors 110a, 110b can include LCD display panels or other types of displays; and the computer 106 does not necessarily have to be physically located with the other components but can be connected through network or other longer-range cabling techniques to the various other components of the presentation system 100.

Figure 2:
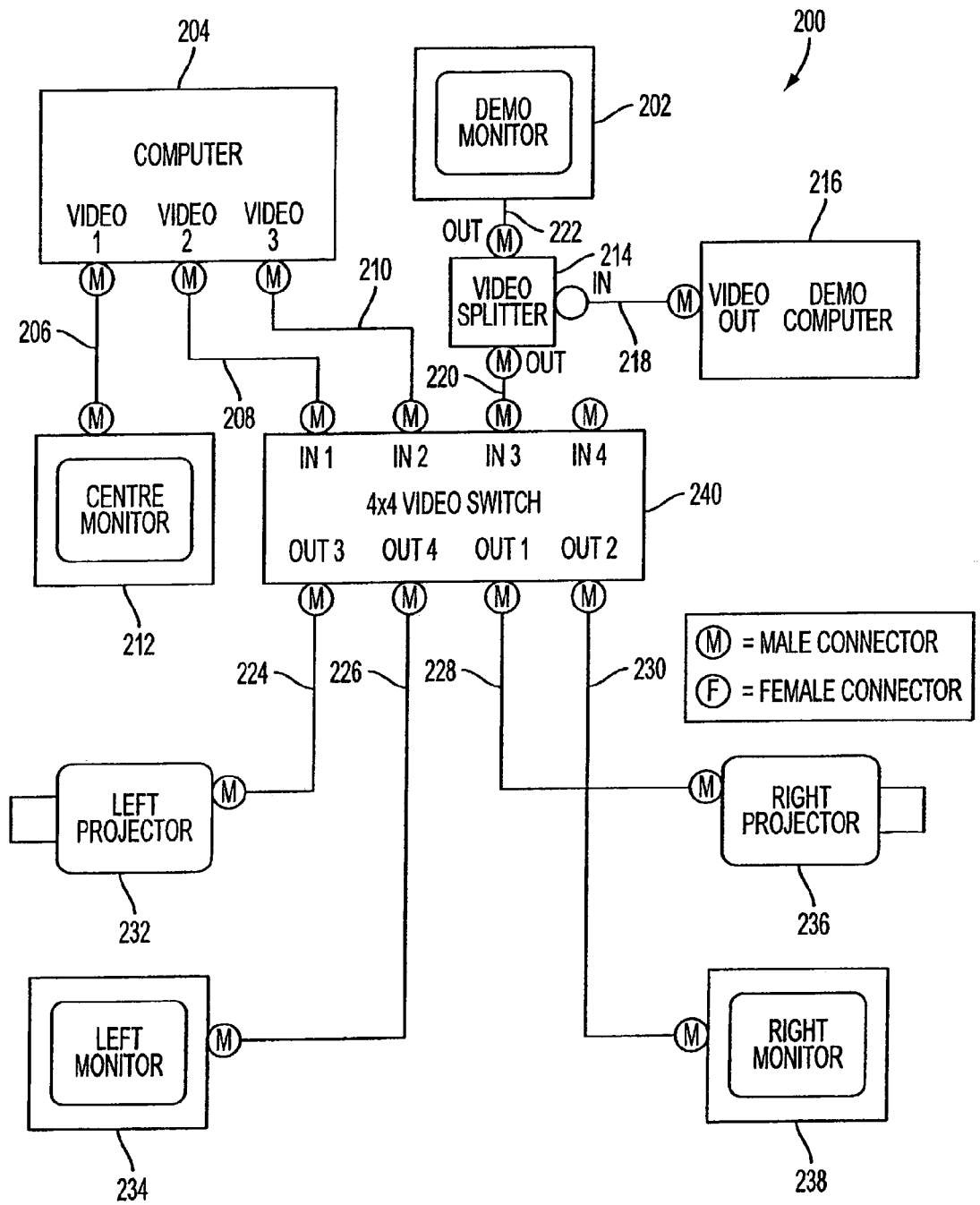
FIG. 2 illustrates an exemplary presentation system according to another embodiment of the present invention.

FIG. 2 illustrates another exemplary presentation system 200 according to another, more preferred embodiment of the present invention. The system 200 utilizes many conventional components to achieve the inventive presentation systems and methods described below. For example, the video switch 240 can be a conventional, controllable 4×4 video switch that includes its own driver software and application programming interface (API) routines for easy integration. Similarly, the monitors 212, 238, 234 can be conventional touch-screen monitors that include their own driver software and calibration routines that easily integrate with other components of the system 200. Modern operating systems, such as the one executing on computer 204 typically allow defining of multiple video displays so that no modification of the operating system is needed to support operation and interaction of multiple video cards within the computer 204.

Within this embodiment, as compared to system 100, additional video displays are possible and a video switch 240 is used to provide additional functionality. However, because many aspects of the system 200 are similar to those of the system 100 of FIG. 1, detailed explanation of some features are not repeated when describing FIG. 2.

The system 200 includes a computer 204 used by a presenter to provide a multi-screen presentation to an audience using left 232 and right 236 projectors. The presenter has available three monitors: a left screen monitor 234 which shows the material being presented from the left projector 232, a right screen monitor 238 which shows the material being presented from the right projector 236, and the center monitor 212 which provides a graphical user interface to the presentation software application running on the computer 204.

In the exemplary system 200, there is also a demonstration computer 216, demonstration monitor 202, and video splitter 214. The video splitter 214 provides the video output 218 from the demonstration computer 216 to both the demonstration monitor 202 and the video switch 240. The demonstration computer 216 is typically under the control of the presenter and can be used to create simulations and other demonstrations that further augment or explain the presentation materials being viewed by an audience. Consequently, the graphical user interface also allows the presenter to direct the video output of the demonstration computer 216 to one of the projectors 232, 236 so that the audience has the benefit of the simulations and demonstrations.

The video switch 240 is a conventional video switch as is known to one of ordinary skill and can be controlled to direct a data signal received at one of its inputs to one or more of its data outputs. As shown, the video switch 240 receives at least three video signals: a) 208 (from the computer 204); b) 210 (from the computer 204); and c) 220 (from the demonstration computer 216 via the video splitter 214). Depending on the settings of the video switch 240, these various input signals are then directed to one or more of the following outputs: a) 224 (the left projector 232); b) 226 (the left monitor 234); c) 228 (the right projector 236); and d) 230 (the right monitor 238).

Similar to the system 100 described before, the system 200 of FIG. 2 provides a presentation system that allows a presenter to use a graphical user interface that executes on computer 204 and displays on the center monitor 212. This user interface permits the presenter to retrieve presentation materials, preview them on the center monitor 212 and then dispatch the materials to either the left projector 232, the right projector 236, or both. To control what is presented to the audience, the presenter uses the interface to send materials out of one of two video outputs 208, 210 and to configure the video switch 240 to direct its different video inputs to appropriate video outputs.

Figure 3:
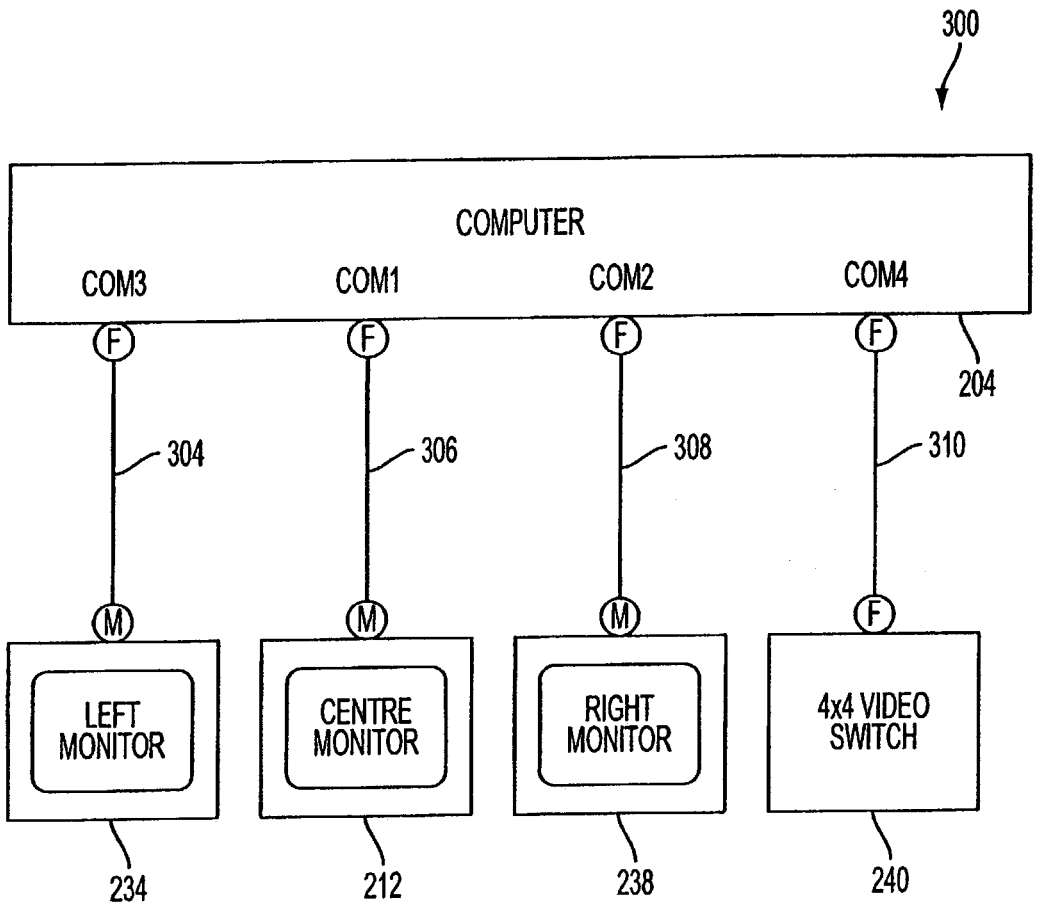
FIG. 3 illustrates additional connections useful in the presentation system according to the embodiment of FIG. 2.

As shown in FIG. 3, the serial path 310 is one exemplary method for the computer 204 to selectably configure the video switch 240. In particular, using the communications link 310, the presenter interacts with the presentation system software to send a command from the computer 204 to the video switch 240. Based on this command, the video switch 240 controls the coupling between video inputs and outputs.

The right monitor 238, left monitor 234, and the center monitor 212 in a preferred embodiment are all touch-screen monitors. In addition, the computer 204 is executing three instances of an annotation tool (e.g., a software application) wherein each instance of the annotation tool allows modification or augmentation of the video data displayed on a respective one of the monitors 212, 234, 238. This augmented video data is overlaid onto any presentation slides that are currently being displayed. As shown in FIG. 3, these monitors are connected to respective inputs of the computer 204. The exemplary feedback paths 304–308 of FIG. 3 are shown as serial communication paths that provide responses to the computer 204 that are dependent on tactile interaction with a respective touch-screen monitor. The feedback data is routed to the appropriate instance of the annotation tools in order to appropriately adjust the video data displayed on the appropriate monitor.

In operation, the presenter will touch one monitor for example, right monitor 238 which brings the "focus" of the operating system to the instance of the annotation tool associated with the right monitor 238. Using the annotation tool and the touch screen monitor 238 (along with its driver software), the presenter is able to draw such things as text, boxes, free-hand diagrams and other annotations that can be overlaid onto the video data that is being output by the computer 204 for display on the right presentation screen. Accordingly, the audience has the benefit of static presentation material that can be easily augmented in real-time in response to the individual needs of that particular audience.

Figure 4:
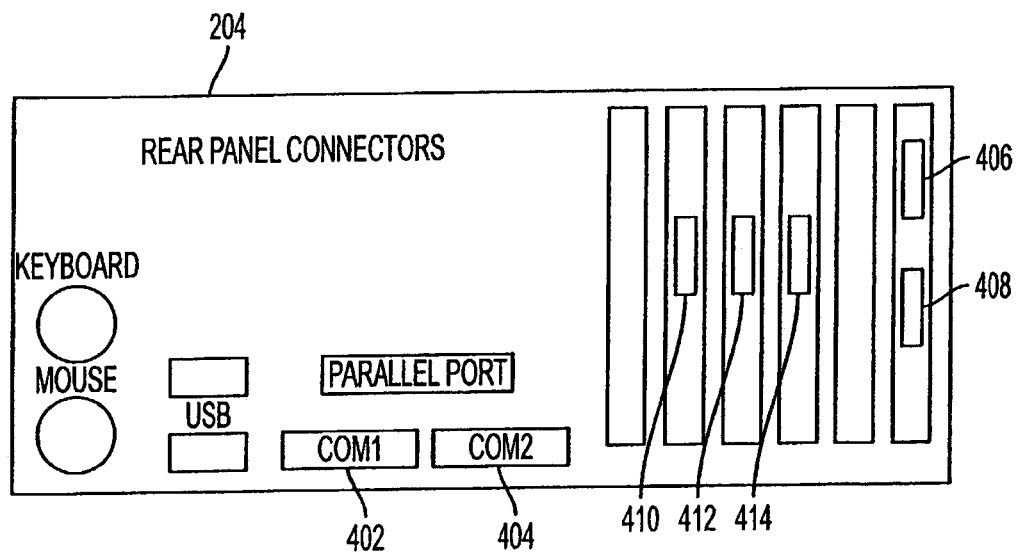
FIG. 4 illustrates rear panel connectors of an exemplary computer according to an embodiment of the present invention.

FIG. 4 displays an exemplary view of a computer 204. As shown, this computer can include multiple video output ports 410–414 as well as multiple input/output ports 402–408. The present invention is not limited to the specific computer arrangement and port types of FIG. 4, but rather contemplates alternative, functionally equivalent arrangements as well.

Figure 5:
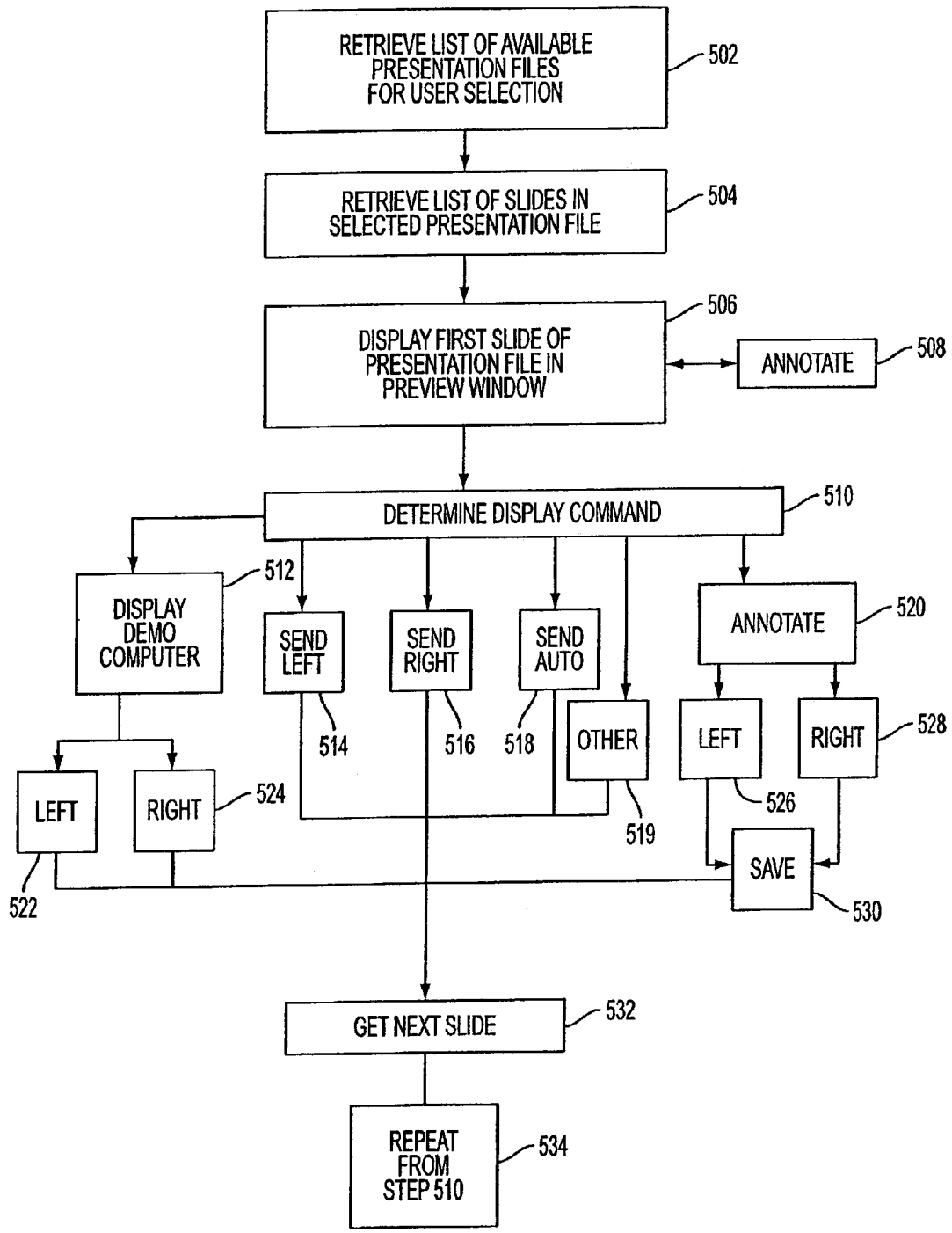
FIG. 5 depicts a logical flowchart of an exemplary presentation method according to an embodiment of the present invention.

FIG. 5 depicts a high-level logical flowchart of an exemplary presentation method according to an embodiment of the present invention. According to this flowchart, the presenter can utilize a system such as that depicted in FIG. 2 to provide effective and dynamic multiple-screen presentations to an audience. The method can be embodied as one or more software applications that can run on one or more computers that when executed perform the presentation method as herein described.

In step 502, a list of available presentations are presented to a presenter to allow the presenter to make a selection. Once a presentation file is selected, the method continues, in step 504, by providing a list of the slides that comprise the selected presentation. Once the presentation file is selected, the presentation system can proceed with the later steps of displaying images under the control of the presenter. However, a preloader is one useful tool that preloads images and the accompanying data files so that they are cached prior to the start of the presentation. In operation, the preloader tool may or may not be used at the discretion of the presenter; however, use of the cached images will allow faster display of different screens as compared to performing the presentation with uncached images.

The first slide among the slides is automatically presented in a preview window, in step 506, so that the presenter can see what the next slide is and decide how it can best be displayed. At this point, the presenter might determine that the slide should be annotated, in step 508, before being displayed.

Next, in step 510, the method determines which of many possible alternatives the presenter selects for the display of the preview slide. For example, the presenter might select, in step 514, to send the preview slide to the left screen or, in step 516 to send the preview slide to the right screen. Alternatively, the method can include an automatic dispatch feature that refers to a preference file to determine, in step 518, which screen to automatically forward the preview slide to. Other display options can be selected in step 519, these options can include such things as blanking the left or right screen, going back one slide in the presentation, skipping the current preview slide without displaying it, jumping to a slide out of order, jumping to a slide from another presentation file, or sending a blank template to one of the display screens. The presenter can also select, in step 512, to display the output of a demonstration computer on either the left screen (step 522) or the right screen (step 524). The presenter can also elect, in step 520, to annotate the slide that is displayed on either the left screen (in step 526) or the right screen (in step 528). By annotating a slide, the presenter is able to interactively augment the presentation in a customized manner appropriate for the audience at hand. As the annotations may be useful in later slide presentations and in order to preserve annotations to more than one displayed slide, step 530 of the method saves any annotations for future use. Based on the presenter's selection for displaying or annotating a presentation slide, step 532 results in the next slide being retrieved and displayed in the preview window. Step 534 represents that the method then repeats itself from step 510 until the last slide of the presentation file is displayed. The details of this method are presented below in relation to a specific interface and software application for controlling a slide presentation.

Figure 6:
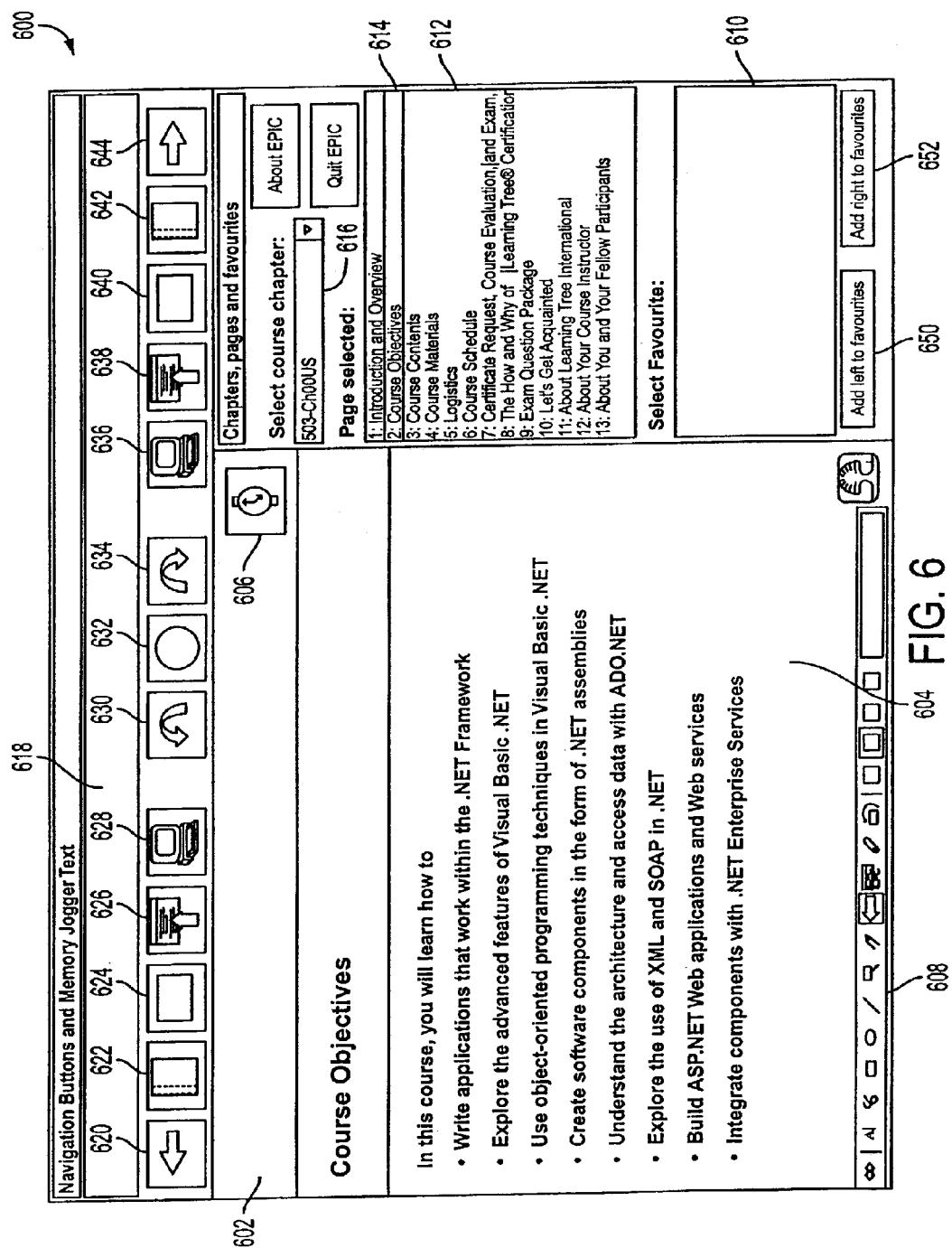
FIG. 6 illustrates an exemplary screenshot of a presentation application interface according to an embodiment of the present invention.

FIG. 6 shows an exemplary screen shot 600 of the presentation software application that executes on the computer 204 that allows the presenter to control the presentation made to an audience. Graphical user interface components such as drop-down menus, selection boxes, icons, display windows, toolbars, and manipulations thereof are well known in the art and will not be described in great detail.

The foundation for a presentation can consist of, for example, a number of PowerPoint slides arranged together in what can be referred to as a presentation file. Other slide formats are also contemplated within the present invention. The PowerPoint files, or slide shows, and their individual frames, can be stored on the hard disk drive of the computer 204. For example, the presentation software can be set to look for a presentation files in a default directory such as "D:\courses". Within that directory would be a number of different presentation files that the presentation software automatically scans and displays to the presenter for selection thereof.

In one embodiment, the presentation system also permits user-defined preference data to be associated with any one of the presentation files. This preference data can take the form of preference files using a predetermined extension (e.g., ".ipf") so that the presentation software can easily associate a preference file with its similarly named presentation file. In a preferred embodiment, the preference file can contain a number of entries having three fields:

<Slide Number>, <Direction Tag>, <Memory Jogger Text>

Thus, a preference file could resemble:

14, R, Mention all three aspects

2, L,

. . .

16, R, Tell joke about the three programmers

As shown, there is no need for the slide numbers to be in numerical order, although following such a convention may prove helpful under certain circumstances. Furthermore, there is no requirement that each slide have an entry nor that each entry have data in every field.

Alternatively, the preference information can be included in slides of the presentation file itself. Using the "notes" section of a PowerPoint slide, or similar features for other presentation file formats, the preference information does not need to be stored in a separate preference file but can be included within the presentation file.

The presentation software interface provides a drop-down box 616 that assists the presenter in selecting a presentation. In FIG. 6, for example, the presenter has selected a file named "503-CH00US" which, in one embodiment, can be meaningful and indicate that the presentation pertains to chapter 00 of lesson 503. On the hard drive this file could be stored as a PowerPoint file "503-Ch00US.ppt". In a preferred embodiment, the first slide of a selected presentation is automatically displayed in the preview window 602.

The window 612 shows the 13 slides within the selected presentation file and their respective titles. One slide title 614 is shown as selected (as indicated by the reverse video) and this slide 604 is displayed in the preview window 602. From this window 602 the presenter can direct (or dispatch) the slide 604 to one of the video outputs of the computer 204.

The monitor on which the screen 600 is displayed can be a touch-screen monitor 212 but the presenter can also interact with the presentation software's interface using a keyboard or mouse in addition to tactile input.

There are three icons in screen 600 that determine the destination of the preview slide 604. The term "destination" refers to which video output of computer 204 the slide is sent so that it is displayed on either the left or right screen. According to one embodiment, the set-up and cable connections of the video switch are configured in a predetermined manner such as that shown in FIG. 2. The presentation software knows of this predetermined configuration and is itself configured to provide slide to the appropriate video output based on which icon is selected by the presenter. The specific cabling connections can be different than that shown in FIG. 2 as long as the presentation software is configured to direct video output accordingly.

The icon 620 causes the presentation software to send the preview slide 604 to the left screen, while the icon 644 causes the presentation software to send the preview slide 604 to the right screen. If the preview slide 604 has a direction preference specified in an associated preferences file, then the icon 632 becomes active and, by selecting that icon 632, the presenter can send the slide to the preferred screen based on the direction preference found in the preference file. Once the preview slide 604 is sent to its appropriate screen for display, the presentation software automatically displays the next slide in the sequence of slides within the window 602. The preference tag can be overridden by using either icon 620 or 644 instead of the automatic icon 632. The window 618 is used for displaying any memory jogger text from the preference file to assist the presenter with the presentation.

According to one embodiment of the present invention, a slide's entry in the preference file can have a direction entry such as "LR". This double entry will have the effect of automatically displaying the one slide on the left screen and then displaying the next slide on the right screen so that both slides appear to be displayed substantially simultaneously. As a result, the eventual new preview slide is two removed from the initial preview slide.

Slides can be selected out of sequence from the display window 612 and then displayed in the preview window 602.

The interface screen 600 also provides a "go-back" icon 630 and a "go-forward" icon 634. The icon 630 allows the presenter to proceed in a reverse direction in the preview window 602 and the icon 634 allows the current preview slide 604 to be skipped and the next slide in the presentation to be displayed in the preview window 602.

The icons 626 and 638, respectively, provide a left screen and right screen "slide jog" feature that allows a slide to appear to be slid up the display screen. This activity mimics the traditional action of a presenter who slides a view foil up on the projector so that the bottom half of the foil is emphasized. These icons act as toggles such that successive selection of the icon flips between normal presentation of a slide and "jogged" presentation of the slide.

In order to focus students on one screen or the other, and for additional reasons within a presentation, the presentation software interface provides icon 624 to blank the left display and icon 640 to blank the right display. Selecting either of these icons again will result in the appropriate display being "unblanked".

As shown in the environment of FIG. 2, the video output from the demonstration computer 216 is provided to the video switch 240. The presentation software can effect the display of this video output to one of the display projectors 232, 236 by appropriate control of the video switch 240 via the communications link 310. When the presenter wants to direct the output from the demonstration computer 216 to the left projector, the icon 628 is selected. This selection causes the presentation software to control the video switch 240 to display the video signal 218 on the left screen. Similar functionality with the right projector 236 is accomplished using the icon 636. A second selection of either of the icons 628, 636 will restore the displayed slides to the respective screen instead of the output from the demonstration computer 216. A second demonstration computer can be included that takes advantage of the unused fourth input of video switch 240. In such an alternative, manual control of the video switch 240 can prove useful in selecting appropriate video signal routing.

Using the buttons 650, 652, respectively, the current slide displayed on the left or right display screen can be added to a "favorites" list displayed in window 610. This list can be named something meaningful such as "favorites.fvt" and located in the default directory "D:\courses". Other file names and locations could also be used.

In a preferred embodiment, the format of the file is:
<Presentation File>, <Slide Number>: <Descriptive Text>

Accordingly, one entry may resemble:
409-Ch05, 14: Free Threading which refers to the fourteenth slide of the presentation file 409-Ch05.ppt (for example, if PowerPoint slides are being used). The descriptive text can be any text, but the slide title is one useful example.

By selecting either of the buttons 650 or 652, a new entry is appended to, or otherwise inserted into, the favorites file. In a preferred embodiment, this file is useful among different presentation files and is not specific to a particular presentation file. The presenter selects a slide from the window 610 similar to the manner in which a slide is selected from the window 612. One difference, is that the presentation software must open the referenced presentation file, extract the appropriate slide and display that in the preview window 602. The slide can then be dispatched to the left or right screen using the icons 620 and 644 respectively. Once the slide is dispatched, the presentation reverts back to the slide location within the original presentation file in order to select the next slide to place in the preview window 602.

The presentation software cooperates with three different instances of a slide annotation application (i.e., an annotation tool). The slide annotation tool can be a vector-based drawing tool that generates graphics that can be overlaid onto a presentation slide. Each of these instances of the annotation tool correspond to a different one of the monitors 212, 234, 238. The execution of an annotation tool instance results in an annotation toolbar being displayed on each of the different monitors 212, 234, 238. The annotation toolbar 608 associated with the annotation tool for the center monitor 212 is depicted at the bottom of the preview window 602. Using this toolbar, the presenter can annotate the slide 604 before it is dispatched to either the left or right display screens. Each of the left and right monitors 234 and 238 have their own associated annotation tools and similar toolbars.

The clock icon 606 opens a timer window that allows a presenter to select a time period and display a countdown screen that indicates remaining time within that period. This time period can reflect the time left to complete an exercise or the time left until the end of a break in the presentation.

Figure 7:
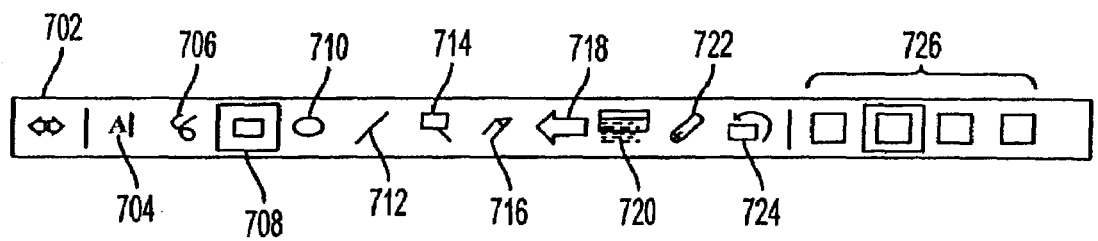
FIG. 7 illustrates an exemplary toolbar of an annotation application for touch-screen monitors according to an embodiment of the present invention.

FIG. 7 depicts an exemplary annotation toll toolbar such as that shown in FIG. 6. The different functions of the toolbar are selected by tapping or selecting the appropriate icon. From left to right, the icons include:

702: A hide/unhide button that expands or contracts the display of the toolbar.

704: A text function that is used by tapping on the presentation slide where text should appear and then using the keyboard (of the computer 204) to enter text.

706: A free-hand drawing tool that allows drawing on the slide, preferably using a stylus or other similar implement.

708: A rectangle draw function that allows selecting a starting corner and dragging to an ending corner to define a rectangle.

710: An ellipse draw function similar to the rectangle function but an ellipse is drawn in the defined "boundary" box.

In a preferred embodiment, both the rectangle and ellipse tools automatically activate a text entry function so that the created shape can have text entered without requiring the selection of any additional icons.

712: A straight line draw function that is used by selecting the starting and ending points of the line.

714: A "callout" function that creates a text entry box that resembles a comic strip dialogue balloon.

716: A highlighter tool that creates a rectangle on the screen that is highlighted in transparent yellow.

718: A pointer tool that allows an indicator to be displayed on the presentation slide at a desired location. In a preferred embodiment, the indicator is a bright red arrow. This arrow will move to any location on the presentation slide that is tapped by the presenter.

720: A progressive revelation function that covers portions of the presentation slide to prevent its display. The first tap on the screen sets the starting vertical location and each successive tap repositions the overlay to display more and more of the presentation slide.

722: An eraser tool that erases any annotations on a presentation slide.

724: An undo function that removes each annotation in a reverse order.

726: A color selection tool that selects from among different colors the color for future annotation operations.

Annotations can be taking place on the left, right and center monitors in any particular order; therefore, in a preferred embodiment, annotations are saved every time a presenter navigates away from a presentation slide. For example, slide 14 can be displayed on the left monitor 234 and be annotated while slide 13 is displayed on the right monitor 238. If the presenter touches the right monitor 238, then the operating system of computer 204 detects that focus has now shifted to the right monitor 238 and any further input will be interpreted by the annotation tool associated with that monitor 238. The presentation software also saves any current annotations for slide 14 before proceeding. If the presenter then navigates back to slide 14, the current annotations for slide 13 are saved and further input is interpreted by the annotation tool associated with the left monitor 234.

In a preferred embodiment, the vector graphics files created by each annotation tool are stored in the "C:\courses" directory. For example, as annotations are made to the slides within presentation file 409-Ch05.ppt, a directory 409-Ch05.ann can be created and populated with a file "xxx" wherein the "xxx" refers to the slide within that presentation file.

When the presentation software presents a slide in the preview window 602 it can automatically search for the existence of any annotation files and automatically augment the slide accordingly. As a result, annotation files can be saved and moved to another computer to augment a presentation from that computer while still utilizing the presentation slides that reside on the second computer. Also, the re-display of an annotated slide is not dependent on the display screen on which the slide was originally annotated. For example, a slide displayed and annotated while on the right display screen can be later recalled for display and dispatched to the left display screen and any previous annotations will be displayed on the left display screen without any need for modification.

Returning briefly to the interface screen 600 of FIG. 6, there are two complementary icons 622 and 642. These icons, respectively, start a blank slide on the left and right display screens. This blank slide can then be annotated as desired. In a preferred embodiment, a dialog box appears that asks for a name for the blank slide and can provide a suggested default name as well. If the newly named slide is not saved as a favorite, then it will be deleted upon ending the current presentation. If it is saved, then it will be available for recall later. In a similar manner, individual slides may be created and copied into the "C:\courses" directory and manually added to the favorites file. In this manner, additional, extrinsic slides that augment a presentation file can easily be made available for selection and display during a pre-scripted presentation.

The presentation system is not limited to presenting viewable content from only a single document file format. The presentation system, for example, can work with two or more different document file formats such as PowerPoint presentations and Adobe Acrobat PDF files. In a preferred embodiment, the PowerPoint presentations are used to deliver screens of information in landscape layout, while Acrobat files display information from portrait layout paginated documents.

According to this embodiment, both the PowerPoint and Acrobat presentations can be treated in exactly the same way by the presentation system, including the incorporation of any annotation files associated with each screen of the document being displayed. Because of the aspect ratio difference between landscape and portrait documents, there may be instances in which only two-thirds of a portrait-mode page (e.g., an Acrobat page) is displayed on each screen and projector. The 'nudge up' buttons 626, 638 on the interface 600 are used to make the lower two-thirds of an Acrobat page visible.

The functionality and benefits of the "favorites" mechanism remain the same for either PowerPoint or Acrobat pages, as both formats can be saved and then recalled for display on any display screen 212, 234, 238.

Figure 8:
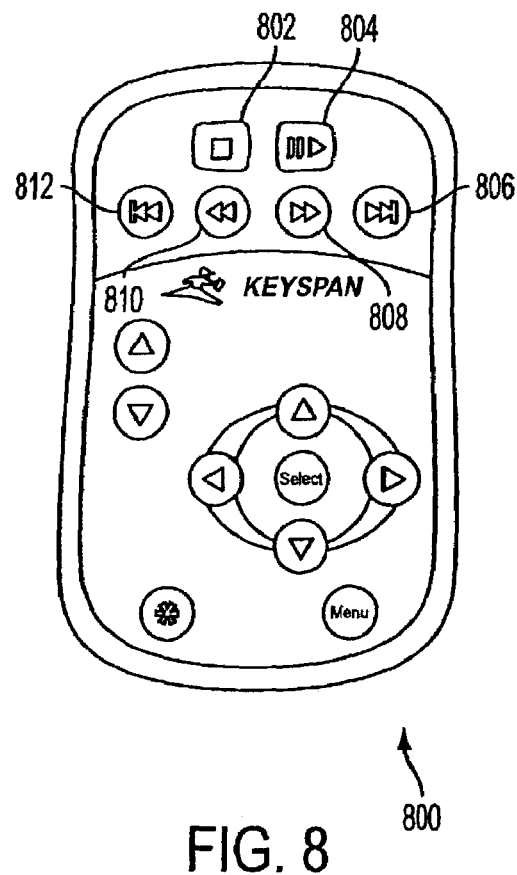
FIG. 8 illustrates an exemplary remote control according to an embodiment of the present invention.

An exemplary remote control 108 of FIG. 1 is shown in more detail in FIG. 8 as element 800. For example, the remote control 800 can connect to the computer 204 using an input/output port that is not being used by another component of the system 200. The remote control does not need to have the entire tool suite that is shown in FIG. 6 but rather can include a button 802 for automatically advancing a slide; a button 804 for skipping the current preview slide; a button 806 for sending the preview slide to the right screen; a button 808 for blanking/unblanking the right screen; a button 810 for blanking/unblanking the left screen; and a button 812 for sending the preview slide to the left screen.

Figure 9:
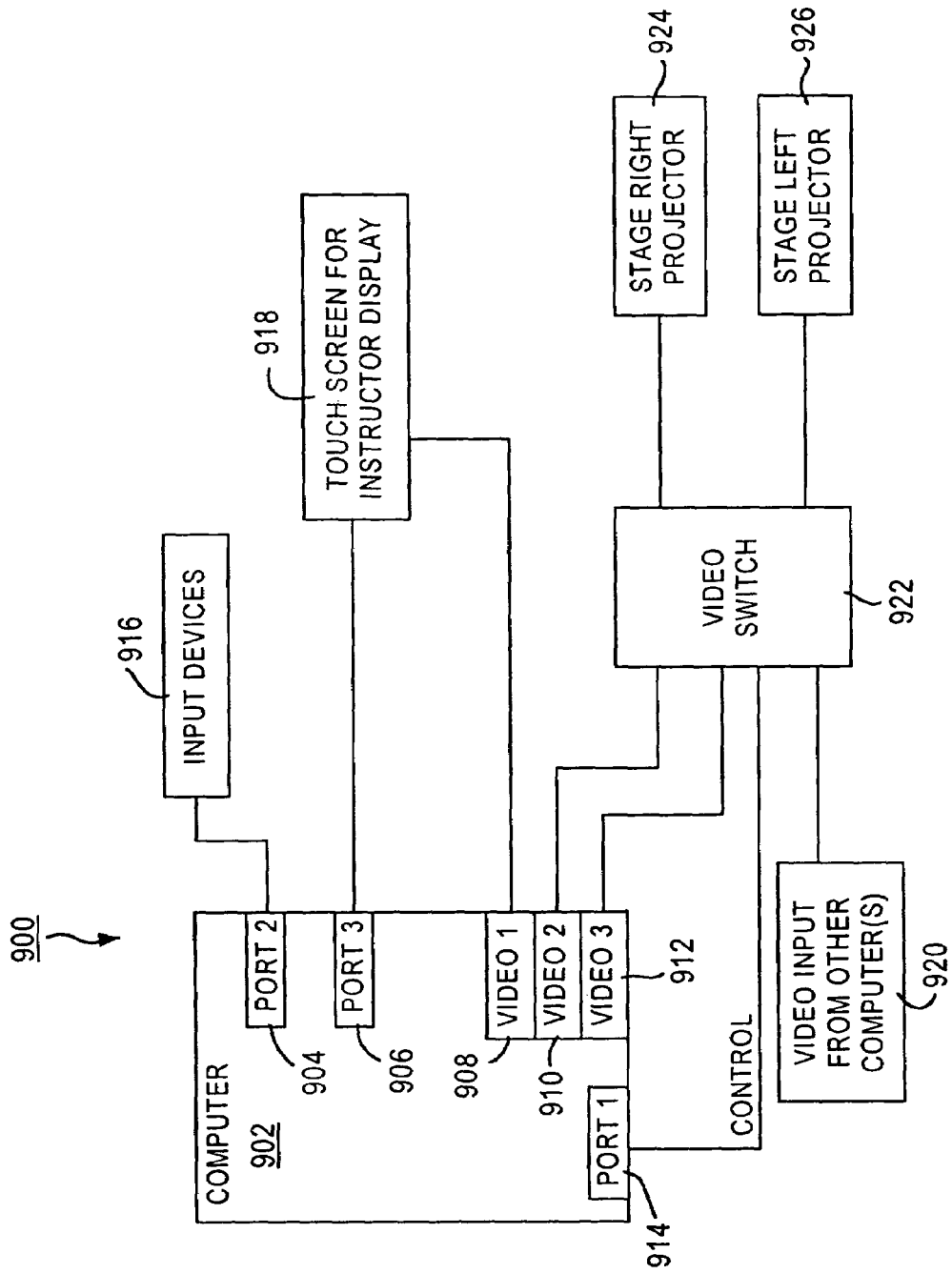
FIG. 9 illustrates an exemplary presentation system incorporating a single touch-screen display.

FIG. 9 depicts an alternative presentation system arrangement 900 as compared to the system 100 of FIG. 1 or the system 200 of FIG. 2. However, there are many common components in each of the systems that have previously been described in detail with respect to the earlier figures. Accordingly, so as not to obscure the differences between the various arrangements, detailed description of those common features shared by each arrangement are not repeated with reference to FIG. 9. Instead, the distinctions between the various arrangements are highlighted and a detailed description of those differences is provided.

In FIG. 9, the computer 902 controls the data flows and presentation materials used by the other components. This computer 902 includes a communications port 904 for interfacing with input devices such as trackball, keyboards (standard or miniature) and mice. The computer 902 provides a graphical user interface, via the video port 908, on the touch screen 918 to assist a presenter or instructor in controlling a presentation. The communications port 906 receives feedback from the touch screen 918 such as provided by a stylus.

While any conventional touch screen terminal can be used, an exemplary touch screen 918 is the 18-inch Wacom Cintiq computer-aided design terminal. This particular terminal includes a tailored stylus that allows a user to rest their hand on the display screen while writing. This functionality improves the accuracy of annotation.

Video ports 910 and 912 provide the video output for display on the right and left projectors 924, 926. As described earlier, the presentation system alternates or otherwise controls the electronic display of information by directing display screens to a particular projector under the control of a presenter using the graphical user interface provided on touch screen 918.

As other video sources 920 may be occasionally displayed on either projector 924 or 926, the video outputs from the ports 910 and 912 are routed through a video switch 922 that is controlled via signals from a port 914 on the computer 902. Thus, using the graphical user interface to produce control signals from the port 914, the presenter can control the directing of slides from video ports 910 and 912 as well as control the selection and deselection of alternate video signals from sources 920.

Although the video switch 922 is depicted as a single n×2 video switch (i.e., having n inputs and 2 outputs), other configurations, such as a pair of 2×1 switches, could also be used. Alternatively, the switch 922 can be omitted if the projectors 924 and 926 have multiple input ports. In this alternative, the control signal from port 914 would directly control the appropriate projector to display a selected input.

One significant difference between the system 900 of FIG. 9 and the earlier-described systems is that a single touch screen 918 is used instead of a center display 104 and left and right displays 110*a*, 110*b*. To accommodate this simplification, the presentation control software running on the computer 902 uses a multi-windowed, tabbed interface on the single touch screen 918.

Figure 10:
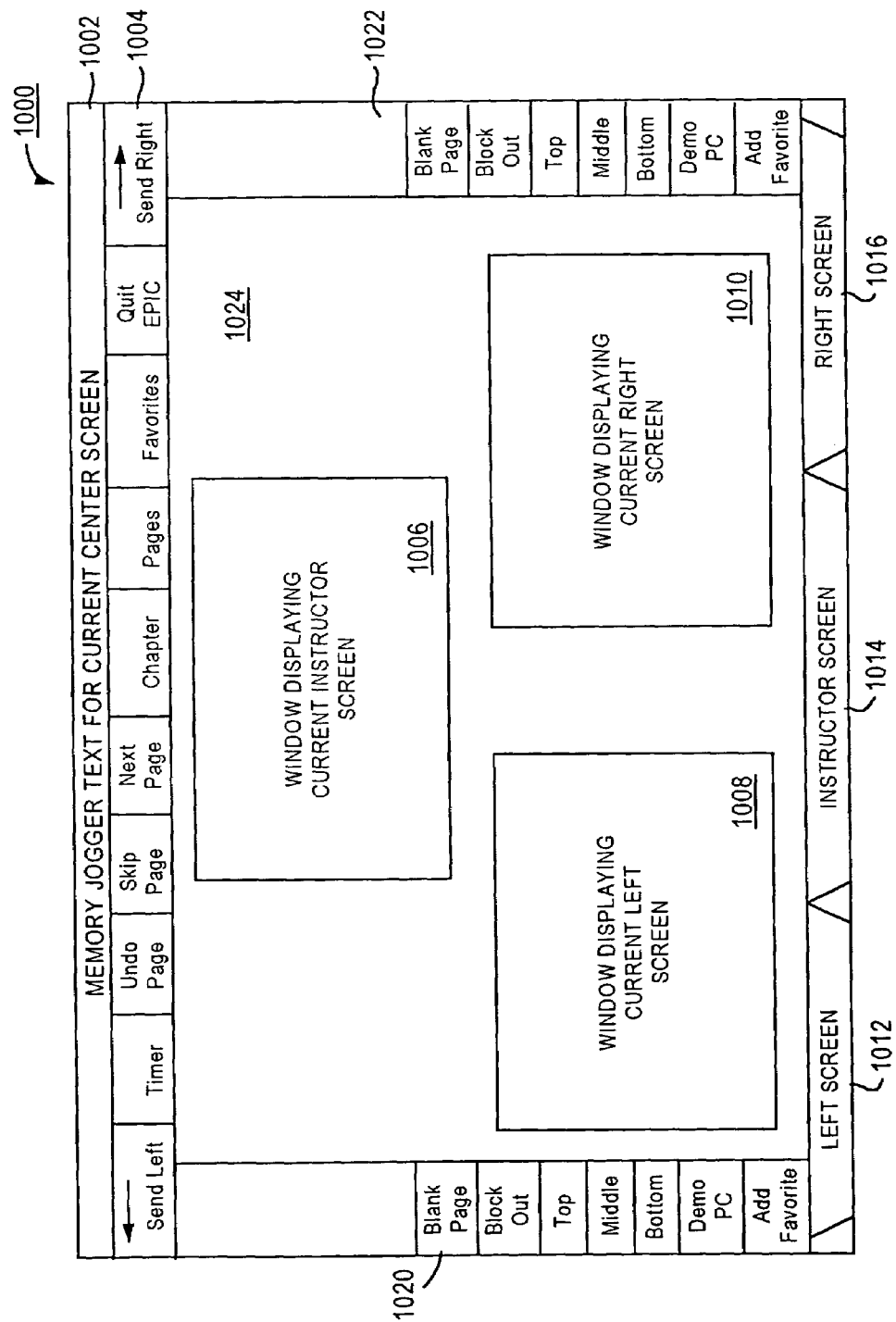
FIG. 10 illustrates an exemplary multi-window interface according to the embodiment of FIG. 9.

FIG. 10 depicts an exemplary graphical user interface 1000 for the single-screen alternative of FIG. 9. The interface 1000 includes a main display area 1024 that includes three sub-windows 1006, 1008, 1010. The center window 1006 displays the current instructor's screen that will be directed to either the left or right projector. The left window 1008 displays the currently displayed left projector screen and the right window 1010 displays the currently displayed right projector screen.

The interface 1000 includes the icon tool bar 1004 across the top as well as respective left and right toolbars 1020 and 1022 along each side. These toolbars provide functionality as described previously that permit a presenter to, for example, direct pages to one screen or the other, skip pages, send blank pages, scroll pages jump between pages, select an alternative video source (e.g., a demo computer), and save or select "favorites". Along the top of the interface 1000 is the memory jogger bar 1002 that displays a brief note about the current instructor screen 1006.

Along the bottom of the interface 1000 are three tabs 1012–1016 corresponding to a respective one of the sub windows in the display area 1024. Using the left screen tab 1012, a user can select the left projector screen for annotation, and using the right screen tab 1010, the user can select the right projector screen for annotation. Using the center tab 1014, the user can return to the composite, multi-windowed screen 1024 shown in FIG. 10.

The graphical user interface 1000 is displayed on the touch screen display 918 that provides feedback to the computer 902 through the communications port 906. Annotations and toolbar selections can be performed from the composite screen 1024; however, selecting one of the current display screens 1008, 1010 will allow finer control over any annotations. One of the display screens can be selected using the appropriate tab (1012 or 1016) or simply by selecting one of the windows (1008 or 1010) using one of the input devices 916.

Figure 11:
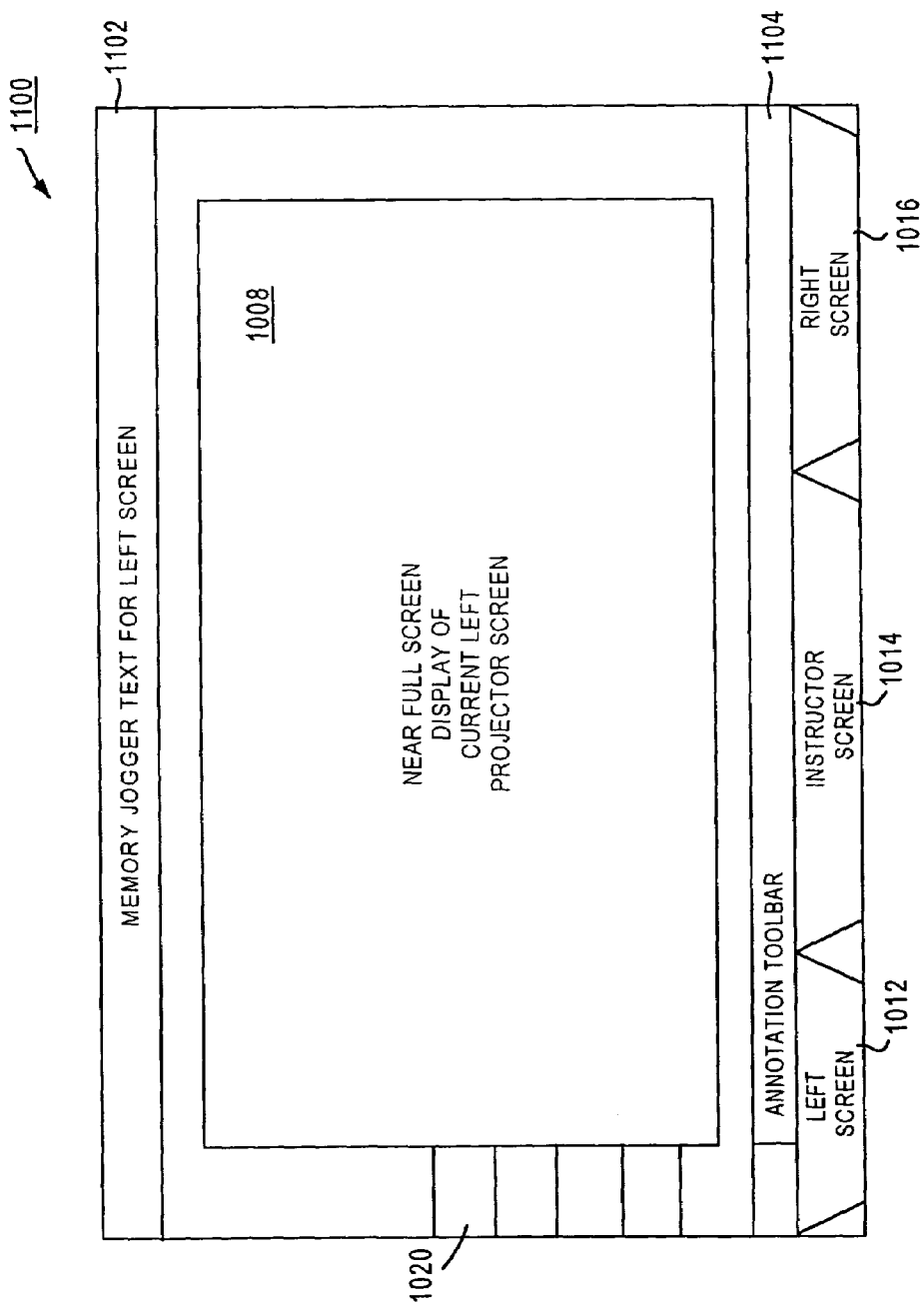
FIG. 11 illustrates an exemplary annotation screen interface according to the embodiment of FIG. 9.

FIG. 11 depicts an exemplary snapshot 1100 of the graphical user interface 1000 once the left screen 1008 (for example) is selected for annotation. As shown in FIG. 11, the screen tabs 1012–1016 remain at the bottom of the snapshot 1100 and the left screen side toolbar 1020 remains to the left side of the snapshot 1100. Instead of the composite screen 1024, however, the current left projector screen is displayed 1008 so as to nearly fill the display area. Along the top of the snapshot 1100 is the memory jogger area 1102 for the current left projector screen and near the bottom of the snapshot 1100 is the annotation toolbar 1104. The details of the annotation toolbar were described earlier with respect to FIG. 7, and its icons provide tools and functions that simplify annotating the currently displayed screen. These annotations appear in real time during the presentation in order to enhance the dynamic nature of a presentation provided using the system 900.

The layout of the snapshot 1100 and the interface 1000 are exemplary in nature. Of course, other functionally equivalent toolbars, screen layout, icon labels, and features are contemplated within additional embodiments of the present invention.

There is much similarity between the tools and facilities available in the alternative presentation system of FIGS. 9–12 and those described and explained with respect to FIGS. 1–8. However, in the alternative arrangement, there is preferably one touch screen for controlling the three video outputs. Thus, a presenter switches form image to image on the touch screen rather than annotating three separate touch screens.

A typical use of this system would start with selecting the "Chapter" button to load a chapter of multiple screens for presentation. Using the instructor screen as the control interface for the presentation application, pages are sent alternately left and right using the left and right buttons of the toolbar. Alternatively, default preferences could be stored that automatically control how the screens are directed for presentation. To annotate a particular projected image, the annotation tools can be used on the smaller display windows found on the instructor screen interface of FIG. 10. Alternatively, should the presenter select one of the current projector screens (by clicking on the window or using the tab button), then the corresponding left or right screen image is magnified to nearly fill the touch screen area as shown in FIG. 11. This allows annotation to be applied much more accurately to the magnified window. Once any annotation is completed, clicking on the "Instructor Screen" tab will cause the composite, multi-windowed instructor screen to reappear so that the presentation can continue.

Figure 12:
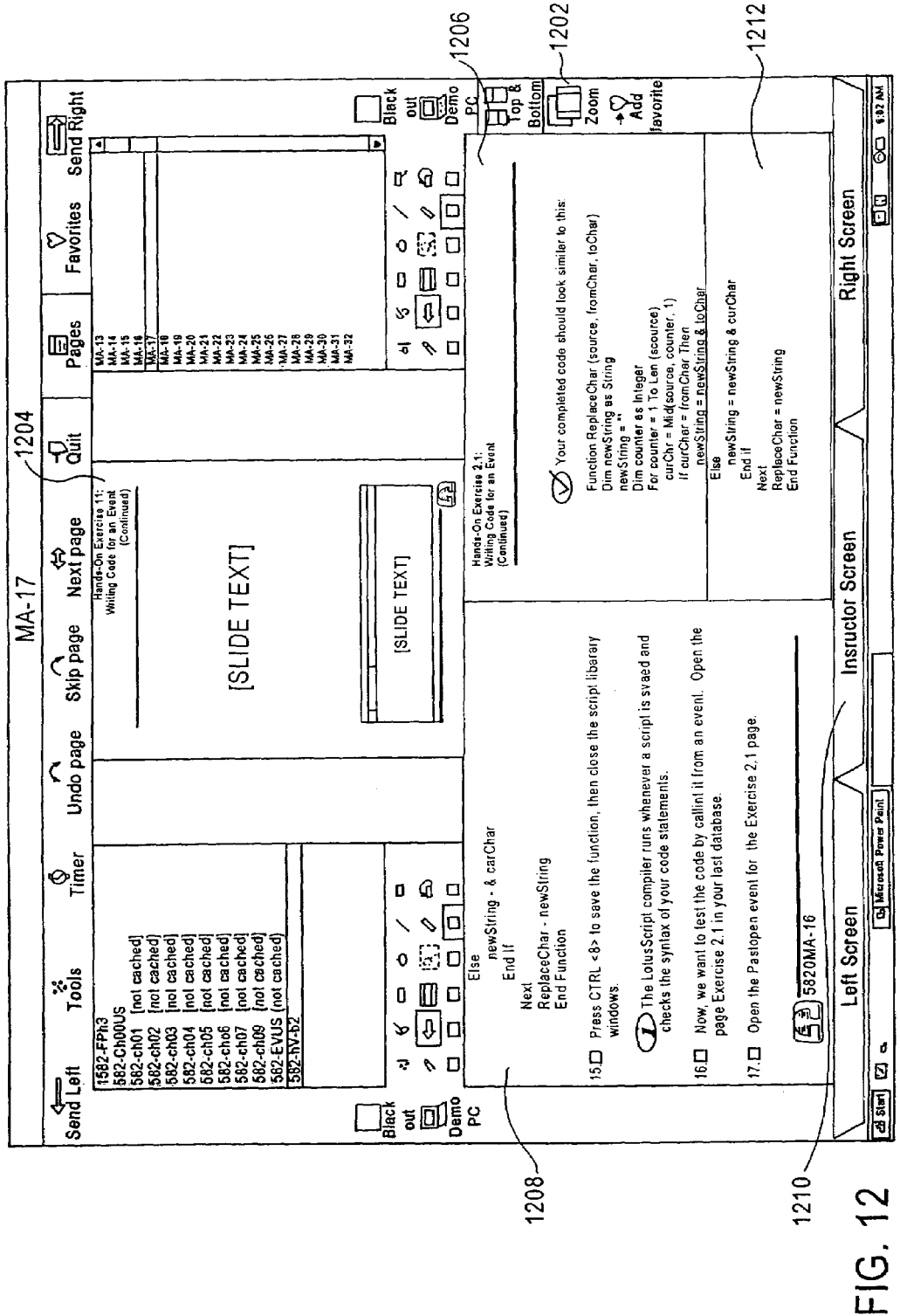
FIG. 12 illustrates an exemplary split-screen mode for displaying a presentation slide according to an embodiment of the present invention.
Figure 13:
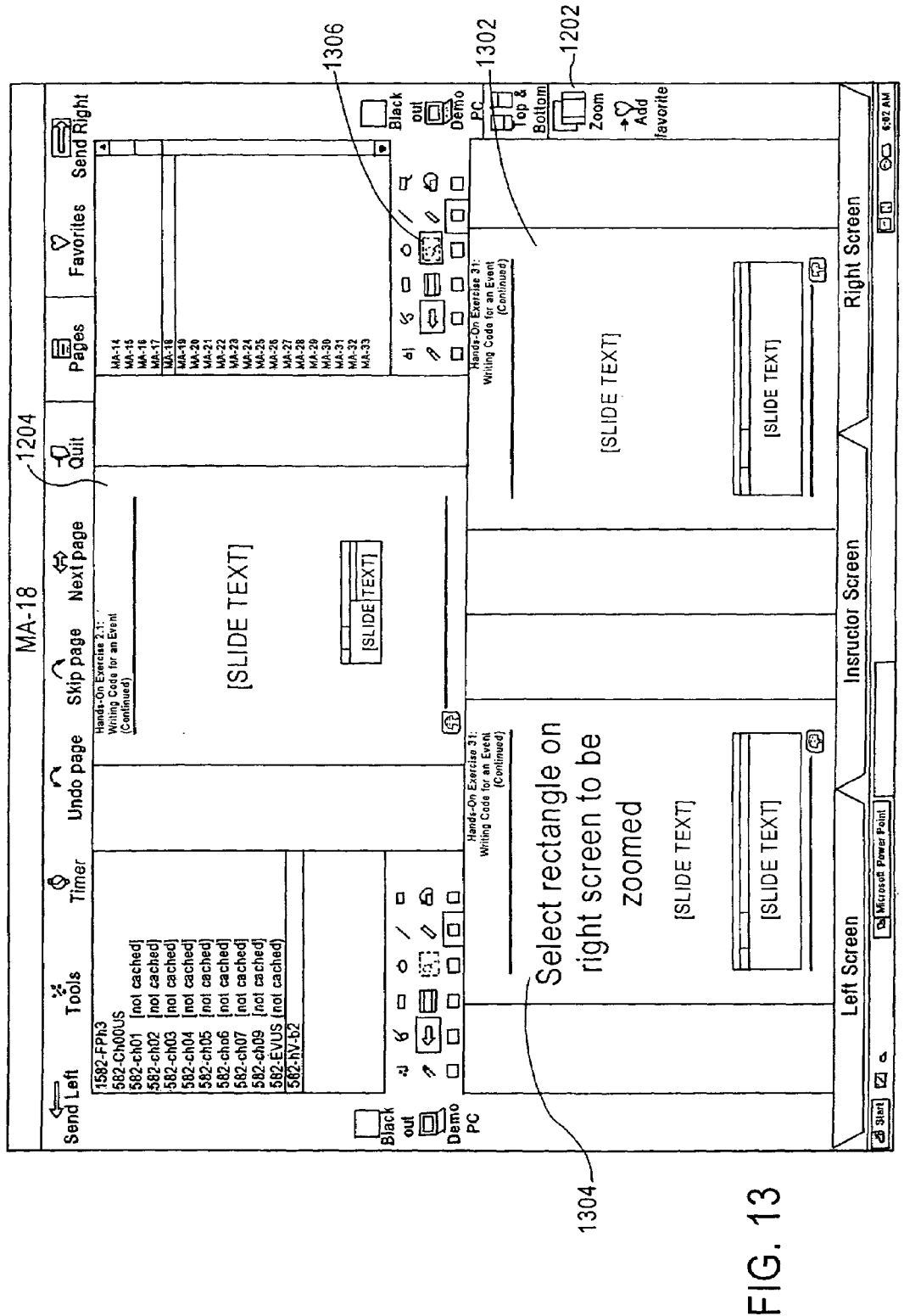
FIG. 13 illustrates an exemplary zoom mode for displaying a presentation slide according to an embodiment of the present invention.
Figure 14:
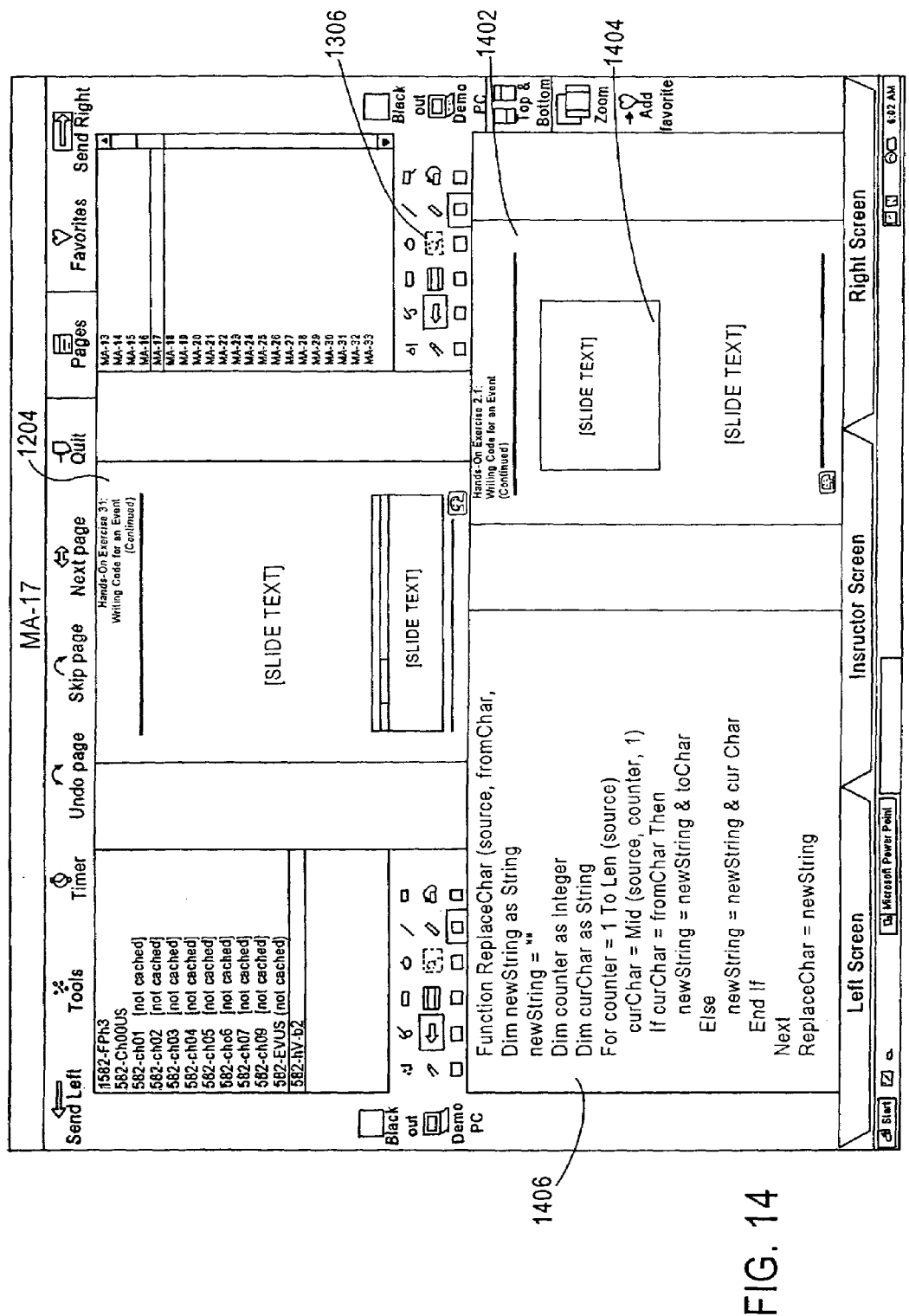
FIG. 14 illustrates the zoom mode display of FIG. 13 after a portion of the presentation slide has been selected for magnification.

FIGS. 12, 13 and 14 illustrate a "zoom" functionality that can be utilized within the multi-display environment of FIG. 1 or the single-screen display environment of FIG. 9. As the functionality is substantially the same in both environments the exemplary embodiment depicted in FIGS. 12–14 is simply that of the single screen display environment. In addition to the scenarios described earlier involving multiple slides displayed on the left and right side screens, the zoom functionality permits displaying a single slide, in different ways, on both the right and left side screens.

FIG. 12 depicts a screen view of an instructor screen as indicated by the tab 1210 at the bottom of the screen. As previously described, this screen displays a next slide 1204 and also a copy 1206 of what is being displayed on the right-hand screen and a copy 1208 of what is being displayed on the left-hand screen.

In the particular situation depicted in FIG. 12, known as split-screen mode, a current slide is displayed on both the left-hand and right-hand screens. For example, the window 1206 shows the upper portion of the current slide while the window 1208 shows the lower portion of the current slide. There is some overlap portion 1212 that appears in both windows and this portion 1212 can be shaded or otherwise visually distinguished to help an observer recognize that this information is in both windows.

A "zoom" tool 1202 is available to the presenter that allows further control of how the current slide is displayed. FIG. 13 depicts how the display windows change once the zoom tool 1202 is selected. While the window 1204 remains the same, the display windows 1304 and 1302 change their behavior.

In the right-hand window 1302, the entire current slide is shown as being displayed on the right side display screen. In a preferred embodiment, the left side display screen is blank. However, the left-hand window 1304 can include helpful instructions for the presenter that suggest, for example, that a portion of the slide should be selected so as to permit "zooming-in". In practice, the presenter would then use the select tool 1306 to select a portion of the slide displayed in window 1302. This tool preferably utilizes a click-and-drag operation that is familiar to most computer users.

FIG. 14 depicts how the windows change once a portion 1404 of the slide 1402 has been selected with the tool 1306. In particular, the left side display screen is no longer blank but displays a "zoomed-in" portion of the slide as shown in the left-hand window 1406. The display of the slide in window 1402 also changes to include some visual cues, such as shading, that highlight the selected portion 1404. The window 1204 continues to show the next slide in the presentation.

As for annotation, both the left-hand window 1406 and the right-hand window 1402 can be annotated using the tools and methods described earlier.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

We claim:

1. A system providing electronic presentations comprising:
   a plurality of presentation slides stored in a first memory accessible by a programmable computer;
   a first display screen coupled with the programmable computer and having a first video input signal;
   a second display screen coupled with the programmable computer and having a second video input signal;
   a third display screen coupled with the programmable computer and having a third video input signal;
   a presentation control application stored in a second memory accessible by the programmable computer; and
   the programmable computer being configured to execute the presentation control application to provide an interface, displayed on the third display screen, by which each of the plurality of slides is dispatched for display to either one of the first or second display screens, wherein said interface is configured to simultaneously display:
   a first window displaying a first image corresponding to the first video input signal;
   a second window displaying a second image corresponding to the second video signal; and
   a third window displaying an image of a next presentation slide.

2. The system according to claim 1, wherein the plurality of slides are arranged in a presentation file.

3. The system according to claim 2, further comprising:
   a plurality of presentation files stored in the first memory; and
   wherein the presentation control application is further configured to:
   display a list of the plurality of presentation files via the interface, and
   select one presentation file based on input received via the interface.

4. The system according to claim 2, further comprising a preference data associated with the presentation file, said preference data stored in the first memory and including one or more entries, each entry associated with a slide of the presentation file; and
   wherein said presentation control application is configured to automatically dispatch a particular slide to either the first or second display screen based on an entry in the preference data corresponding to that Particular slide.

5. The system according to claim 4 wherein after dispatching the particular slide, the presentation control application retrieves the next slide in the presentation file.

6. The system according to claim 5 wherein the third display screen is a touch-screen device.

7. The system according to claim 6 further comprising:
   a slide annotation application executing on the programmable computer and interfacing with the presentation control application.

8. The system according to claim 7 wherein said interface further comprises a selection mechanism configured to select one of the first, second and third windows for annotation and to initiate the slide annotation application.

9. The system according to claim 8 wherein the third display screen is configured to respectively provide tactile feedback information to the slide annotation application and wherein the presentation control application is configured to modify one of the first and second video input signals based on the respective tactile feedback information and selected window.

10. The system according to claim 9 wherein the slide annotation application is configured to store in the first memory an annotation history file based on the respective tactile feedback information.

11. The system according to claim 10 wherein the presentation control application is configured to retrieve any annotation history file associated with a particular slide dispatched for display and display of that particular slide on any of the first, second or third display screens is modified according to the annotation history file.

12. The system according to claim 1, further comprising:
    a video switch having a plurality of inputs coupled with said programmable computer and a plurality of outputs coupled with said first and second display screens, said video switch configurable to selectably couple any of its inputs to any of its outputs.

13. The system according to claim 12, further comprising:
    a demonstration computer providing demonstration video output coupled with a particular one input of the video switch wherein the presentation control application is configured to direct the demonstration video output to either of the first or second display screens.

14. The system according to claim 1, wherein:
    said first video input signal corresponds to a fall view representation of a current presentation slide;
    said second video input signal corresponds to a magnified representation of a portion of the current presentation slide.

15. The system according to claim 14, wherein said presentation control application further comprises a selection tool for selecting the portion of the current presentation slide.

16. A method for providing an electronic presentation of a plurality of slides using multiple display screens, comprising the steps of:
    displaying a slide, from among the plurality of slides, in a preview window within a presentation control interface on a first display screen;
    receiving input via the presentation control interface indicating whether to direct the slide to a second display screen or a third display screen;
    dispatching the slide for display on the indicated display screen;
    displaying simultaneously with the slide in the preview window within the presentation control interface, a first window corresponding to any slide currently displayed on the second display screen and a second window corresponding to any slide currently displayed on the third display screen, and
    retrieving a next slide for display in the preview window.

17. The method according to claim 16, further comprising the steps of:

retrieving a first list of presentation files, each said presentation file comprising a respective plurality of slides;

displaying on the first screen the first list via the presentation control interface; and selecting one of the presentation files, for the electronic presentation, based on input received in response to the display of the first list.

18. The method according to claim 17, further comprising the steps of:

retrieving preference data associated with the one presentation file;

determining if the received input indicates automatic dispatch of the slide; and referring to an entry in the preference data to determine which display screen to dispatch the slide to.

19. The method according to claim 17, further comprising the steps of:

directing video output from a demonstration computer to either one of the second or third display screens in place of a presentation slide.

20. The method according to claim 19, wherein the step of directing includes the step of:

selectably controlling a video switch which includes one input coupled with the demonstration computer and respective outputs coupled with the second and third display screens.

21. The method according to claim 16, further comprising the steps of:

outputting the slide as first-side video data if the slide is dispatched to the second display screen; and outputting the slide as second-side video data if the slide is directed to the third display screen.

22. The method according to claim 21, further comprising the steps of:

selecting one of the first window and second window via the presentation control interface; and displaying the selected window so as to substantially fill the first display screen.

23. The method according to claim 22, further comprising the step of:

providing an annotation application associated with the first display screen which is a touch screen device.

24. The method according to claim 23, wherein:

the annotation application is configured to receive feedback from the first display screen indicating graphic overlay data associated with a particular slide corresponding to the selected window.

25. The method according to claim 24, further comprising the steps of:

adjusting the first-side video data based on the graphic overlay data, if the selected window corresponds to the second display screen; and adjusting the second-side video data based on the graphic overlay data, if the selected window corresponds to the third display screen.

26. The method according to claim 24, further comprising the step of:

storing any graphic overlay data.

27. The method according to claim 26, further comprising the steps of:

recalling a particular slide for display;

retrieving any stored graphic overlay data associated with the recalled slide;

displaying the recalled slide along with the retrieved graphic overlay data on the preview screen; and dispatching the recalled slide and retrieved graphic overlay data to either the first-side or second-side display screen.

28. A method for providing an electronic presentation of a plurality of slides using multiple display screens, comprising the steps of:

displaying a slide, from among a plurality of slides, in a preview window within a presentation control interface on a first display screen;

receiving input via the presentation control interface indicating whether to display a current slide in split-screen mode or in zoom mode;

displaying simultaneously with the slide in the preview window within the presentation control interface, a first window corresponding to a first portion of the current slide for display on a second display screen and a second window corresponding to a second portion of the current slide for display on a third display screen.

29. The method according to claim 28, wherein in zoom mode, the first portion is the entire current slide and the second portion is a magnified portion of the current slide.

30. The method according to claim 28, wherein in zoom mode, the second portion is the entire current slide and the first portion is a magnified portion of the current slide.

31. The method according to claim 28, further comprising the step of:

receiving input via the presentation control interface indicating a selected portion of the current slide to magnify.

32. A computer readable medium bearing instructions for providing an electronic presentation of a plurality of slides using multiple display screens, said instructions being arranged to cause one or more processors upon execution thereof to perform the steps of:

displaying a slide, from among the plurality of slides, in a preview window within a presentation control interface on a first display screen;

receiving input via the presentation control interface indicating whether to direct the slide to a second display screen or a third display screen;

dispatching the slide for display on the indicated display screen;

displaying simultaneously with the slide in the preview window within the presentation control interface, a first window corresponding to any slide currently displayed on the second display screen and a second window corresponding to any slide currently displayed on the third display screen, and retrieving a next slide for display in the preview window.

* * * * *